(12) United States Patent
Rappin et al.

(10) Patent No.: US 6,576,102 B1
(45) Date of Patent: *Jun. 10, 2003

(54) ELECTROCHEMICAL SENSOR AND METHOD THEREOF

(75) Inventors: Craig Rappin, Long Grove, IL (US); Kiamars Hajizadeh, Buffalo Grove, IL (US); Kelly Mills, McHenry, IL (US)

(73) Assignee: Virotek, L.L.C., Buffalo Grove, IL (US)

( * ) Notice: Subject to any disclaimer, the term of this patent is extended or adjusted under 35 U.S.C. 154(b) by 99 days.

This patent is subject to a terminal disclaimer.

(21) Appl. No.: 09/820,372

(22) Filed: Mar. 23, 2001

(51) Int. Cl.[7] .......................... G01N 27/327
(52) U.S. Cl. .................... 204/403.14; 204/403.01; 204/416; 204/403.02
(58) Field of Search ............... 204/416, 431, 204/433, 434, 412, 403.01–403.15

(56) References Cited

U.S. PATENT DOCUMENTS

| | | | |
|---|---|---|---|
| 3,838,033 A | 9/1974 | Mindt et al. | 205/195 |
| 3,925,183 A | 12/1975 | Oswin et al. | 204/195 |
| 3,979,274 A | 9/1976 | Newman | 435/180 |
| 4,005,002 A | 1/1977 | Racine et al. | 204/195 |
| 4,053,381 A | 10/1977 | Hamblen et al. | 204/195 |
| 4,137,495 A | 1/1979 | Brown | 324/30 |
| 4,169,779 A | 10/1979 | Tataria et al. | 204/195 |
| 4,217,196 A | 8/1980 | Huch | 204/195 |
| 4,225,410 A | 9/1980 | Pace | 204/195 |
| 4,321,123 A | 3/1982 | Nakamura et al. | 204/195 |
| 4,392,933 A | 7/1983 | Nakamura et al. | 204/403 |
| 4,407,959 A | 10/1983 | Tsuji et al. | 435/288 |
| 4,413,407 A | 11/1983 | Columbus | 29/825 |
| 4,418,148 A | 11/1983 | Oberhardt | 435/180 |
| 4,420,564 A | 12/1983 | Tsuji et al. | 204/403 |
| 4,431,507 A | 2/1984 | Nankai et al. | 204/403 |
| 4,432,366 A | 2/1984 | Margules | |

(List continued on next page.)

FOREIGN PATENT DOCUMENTS

| | | |
|---|---|---|
| EP | 0 121 385 A1 | 3/1983 |
| EP | 0 078 590 A1 | 5/1983 |
| EP | 0 078 636 B1 | 5/1983 |
| EP | 0 096 095 A1 | 12/1983 |
| EP | 0 125 137 B1 | 11/1984 |
| EP | 0 136 362 B1 | 4/1985 |
| EP | 0 177 743 B1 | 4/1986 |
| EP | 0 230 472 A1 | 8/1987 |
| EP | 0 230 786 A1 | 8/1987 |
| EP | 0 241 309 A3 | 10/1987 |
| EP | 0 255 291 A1 | 2/1988 |
| EP | 0 127 958 B1 | 3/1992 |

(List continued on next page.)

OTHER PUBLICATIONS

JAPIO abstract of Omron Corp. (JP 03–239958–A).*
Derwent abstract of Omron Corp. (JP 03–239958–A).*
Machine translation of Omron Corp. (Jp 08–247987 A).*

(List continued on next page.)

*Primary Examiner*—Nam Nguyen
*Assistant Examiner*—Alex Noguerola
(74) *Attorney, Agent, or Firm*—Wallenstein & Wagner, Ltd.

(57) ABSTRACT

A sensor (10,110) is provided for determination of various concentrations of one or more components within a fluid sample. The sensor (10,110) includes an injection molded body (12,112), at least two electrodes (30,31,32,130,131,132), an enzyme (57,157), and, if desired, an electron transfer mediator. The body includes a reaction zone (24, 124) for receiving a fluid sample. The electrodes (30,31,32, 130,131,132) are at least partially embedded with in the plastic body (12,112) and extend into the reaction zone (24,124). Also contained within the reaction zone is an enzyme (57,157) capable of catalyzing a reaction involving a compound within the fluid sample.

47 Claims, 3 Drawing Sheets

U.S. PATENT DOCUMENTS

| | | | |
|---|---|---|---|
| 4,474,183 A | 10/1984 | Yano et al. | |
| 4,490,216 A | 12/1984 | McConnell | 204/1 |
| 4,502,938 A | 3/1985 | Covington et al. | 204/412 |
| 4,579,643 A | 4/1986 | Mase et al. | 204/424 |
| 4,591,550 A | 5/1986 | Hafeman et al. | 435/4 |
| 4,654,197 A | 3/1987 | Lilja et al. | 204/403 |
| 4,655,901 A | 4/1987 | Mase et al. | 204/426 |
| 4,682,602 A | 7/1987 | Prohaska | 128/635 |
| 4,711,245 A | 12/1987 | Higgins et al. | 128/635 |
| 4,796,014 A | 1/1989 | Chia | 340/573 |
| 4,810,658 A | 3/1989 | Shanks et al. | 436/172 |
| 4,820,636 A | 4/1989 | Hill et al. | 435/14 |
| 4,836,904 A | 6/1989 | Armstrong et al. | 204/294 |
| 4,900,405 A | 2/1990 | Otagawa et al. | 401/153.16 |
| 4,927,516 A | 5/1990 | Yamaguchi et al. | 204/403 |
| 4,935,105 A | 6/1990 | Churchouse | 204/153.12 |
| 4,935,106 A | 6/1990 | Liston et al. | 204/403 |
| 4,938,860 A | 7/1990 | Wogoman | 204/403 |
| 4,948,727 A | 8/1990 | Cass et al. | 435/18 |
| 4,952,300 A | 8/1990 | Diamond | 204/406 |
| 4,970,145 A | 11/1990 | Bennetto et al. | 204/403 |
| 4,978,503 A | 12/1990 | Shanks et al. | 422/58 |
| 4,995,402 A | 2/1991 | Smith et al. | 128/771 |
| 5,030,310 A | 7/1991 | Wogoman | 156/252 |
| 5,049,487 A | 9/1991 | Phillips et al. | 435/4 |
| 5,120,420 A | 6/1992 | Nankai et al. | 204/403 |
| 5,128,015 A | 7/1992 | Szuminsky et al. | 204/403 |
| 5,140,393 A | 8/1992 | Hijikihigawa et al. | 357/25 |
| 5,141,868 A | 8/1992 | Shanks et al. | 435/288 |
| 5,171,689 A | 12/1992 | Kawaguri et al. | 435/290 |
| 5,338,435 A * | 8/1994 | Betts et al. | 204/406 |
| 5,437,999 A | 8/1995 | Diebold et al. | |
| 5,547,555 A | 8/1996 | Schwartz et al. | 204/418 |
| 5,582,697 A | 12/1996 | Ikeda et al. | |
| 5,639,672 A | 6/1997 | Burd et al. | 436/525 |
| 5,695,949 A | 12/1997 | Galen et al. | 435/14 |
| 5,833,824 A | 11/1998 | Benton | |
| RE36,268 E | 8/1999 | Szuminsky et al. | 205/777.5 |
| 5,985,129 A | 11/1999 | Gough et al. | |
| 6,059,946 A | 5/2000 | Yukawa et al. | 204/403 |
| 6,071,251 A | 6/2000 | Cunningham et al. | 600/584 |
| 6,110,696 A | 8/2000 | Brown et al. | 435/7.6 |
| 6,117,292 A * | 9/2000 | Ahmad | 204/416 |
| 6,129,823 A | 10/2000 | Hughes et al. | |
| 6,206,841 B1 | 3/2001 | Cunningham et al. | 600/584 |
| 6,241,862 B1 | 6/2001 | McAleer et al. | |
| 6,294,062 B1 | 9/2001 | Buck, Jr. et al. | 204/400 |
| 6,360,888 B1 * | 3/2002 | McIvor et al. | 206/305 |
| 2001/0050228 A1 | 12/2001 | Jaeger | 204/403 |
| 2002/0002344 A1 | 1/2002 | Douglas et al. | 600/583 |
| 2002/0003087 A1 | 1/2002 | Chih-hui | 204/400 |
| 2002/0029964 A1 | 3/2002 | Matsumoto | 204/403 |
| 2002/0053523 A1 | 5/2002 | Liamos et al. | 205/787 |
| 2002/0092612 A1 | 7/2002 | Davies et al. | |

FOREIGN PATENT DOCUMENTS

| | | |
|---|---|---|
| EP | 0 255 291 B1 | 6/1992 |
| EP | 0 230 472 B1 | 1/1993 |
| EP | 0 127 958 B2 | 4/1996 |
| EP | 1098000 A2 * | 5/2000 |
| EP | 0 230 472 B2 | 12/2000 |
| EP | 1 098 000 A2 | 5/2001 |
| GB | 2154003 A | 8/1985 |
| JP | 55-10584 A | 1/1980 |
| JP | 57-98853 A | 6/1982 |
| JP | 59-166852 A | 9/1984 |
| JP | 60-211350 A | 10/1985 |
| JP | 61-91558 A | 5/1986 |
| JP | 61-294356 A | 12/1986 |
| JP | 62-137559 | 6/1987 |
| JP | 62-156553 A | 7/1987 |
| JP | 63-3248 | 1/1988 |
| JP | 63-3249 A | 1/1988 |
| JP | 03-239958 A * | 10/1991 |
| JP | 08-247987 A * | 9/1996 |
| WO | WO 86/04926 | 8/1986 |
| WO | WO 86/07632 | 12/1986 |
| WO | WO 88/03270 | 5/1988 |

OTHER PUBLICATIONS

Laboratory Techniques in Electroanalytical Chemistry; pp. 51–61 and 124 (Kissinger and Heineman, eds. 1984) no month available.

International Search Report for PCT/US02/08703 mailed Dec. 6, 2002.

* cited by examiner

ELECTROCHEMICAL SENSOR AND METHOD THEREOF

DESCRIPTION

1. Technical Field

The present invention generally relates to electrochemical sensors and, in particular, to molded electrochemical sensors for detection or measurement of analytes in test samples, such as fluids and dissolved solid materials, and the methods of making and using these sensors.

2. Background of the Invention

Electrochemical sensors are used to determine the concentrations of various analytes in testing samples such as fluids and dissolved solid materials. For instance, electrochemical sensors have been made for measuring glucose in human blood. Such sensors have been used by diabetics and health care professionals for monitoring blood glucose levels. The sensors are usually used in conjunction with a meter, which measures light reflectance, if the strip is designed for photometric detection of a die, or which measures some electrical property, such as electrical current, if the strip is designed for detection of an electroactive compound.

Typically, electrochemical sensors are manufactured using an electrically insulating base upon which conductive inks such as carbon and silver are printed by screen printing to form conductive electrode tracks or thin strips of metal are unrolled to form the conductive electrode tracks. The electrodes are the sensing elements of the sensor generally referred to as a transducer. The electrodes are covered with a reagent layer comprising a hydrophilic polymer in combination with an oxidoreductase or a dehydrogenase enzyme specific for the analyte. Further, mounted over a portion of the base and the electrodes is an insulating layer.

Precision and accuracy of electrochemical measurements to a great extent rely on the reproducibility of the electrode surface area on a microscopic scale. Variations in the morphology of the electrode can result in very significant changes in the electrochemical signal readout. Screen-printing has made significant in-roads in the production of sensors for determining glucose. The wide use of screen-printing stems from the ability to mass-produce relatively inexpensive sensors. The use of metal strips unrolled from large rolls has also been employed to mass produce such sensors.

While many advances have been made in the field of screen printing and conductive ink production, the technology still suffers from poor reproducibility of the electrode surface area, dimensional variations, thickness variations, micro-cracks, and shrinkage due to the repetitive and high temperature curing processes involved in using film printing technology. Loss of solvent during printing is another factor that leads to variations in the thickness of electrodes.

Sensor development using printing technology requires several passes of different conductive inks demanding different screens. Slight variations in positioning the screens can lead to substantial errors in IR drop and the applied potentials. Wear and tear of these screens is another source of error. Also, sensor strip production by screen printing suffers from a high level of raw material waste. Generally, for every gram of ink used, there is a gram of ink wasted. Manufacture of such sensors also involves several lamination processes that add to the production complexity and cost of the final product.

SUMMARY OF THE INVENTION

The present invention is an electrochemical sensor that provides for the determination of various analyte concentrations in a testing sample such as fluids and dissolved solid materials. The sensor is designed to facilitate production in large quantities using reliable and cost effective injection molding manufacturing methods. The present invention includes an injection molded plastic strip or body, at least two electrodes, an enzyme, and if desired, an electron transfer mediator. The body includes a cavity or reaction zone for receiving a fluid sample. The electrodes are at least partially embedded within the plastic body and extend into the reaction zone where they are exposed to a test sample. Also contained within the reaction zone is an enzyme capable of catalyzing a reaction involving a compound within the fluid sample.

Specifically, the device cooperates with an electronic meter capable of measuring the difference between the electrical properties of the electrically conductive electrodes within the device. The device, a sensor, includes at least two, and preferably three, spaced apart electrically conductive electrodes, a body having two ends of insulative material molded about and housing the electrodes, means for connecting the meter to the housing, means for receiving a fluid sample, and means for treating one or more electrodes with one or more chemicals to change the electrical properties of the treated electrodes upon contact with the fluid sample. One end of the housing has the means for connecting the meter and the opposite end of the housing has the means for receiving the fluid sample. The means for connecting the meter is a plug formed in the housing exposing the electrodes outside the body.

The sensor is molded and can be a single, unitary piece or two pieces. In the two piece construction, an end cap is attached to the body. In the single piece construction, the body pivots about a hinge and connects onto itself. Protuberances formed in a portion of the body cooperate with troughs to ensure proper alignment.

A capillary inlet is constructed at one end of the sensor to draw the fluid sample into the body upon contact with the fluid sample. The capillary inlet is molded into the end of the body and is in communications with a reaction zone. This reaction zone is a channel formed in the body about the electrodes and is adapted for reacting with the fluid drawn into the body by the capillary force. While the reaction zone may be formed above or below the electrodes, the preference has been to construct it above the electrodes. The capillary has a vent for relieving pressure.

As noted, the electrodes are molded into the plastic. In one embodiment, the electrodes are conductive wires. In another embodiment, the electrodes are constructed from a metal plate. The electrodes may be coated with a different conductive material to enhance their performance.

Apertures are formed in the body of the sensor to permit the holding of the electrodes during the molding process. Apertures may also be formed in the body to chemically treat one or more electrodes in the reaction zone before or after the molding process. Adding chemicals (e.g., reagents with and without enzymes) changes the electrical properties of the treated electrodes upon contact with the fluid sample. In the preferred embodiment, the enzyme is applied to the outer surface of one of the electrodes. An antibody may also be applied to another of the electrodes. An electron mediator may further be applied to the outer surface of one or more of the electrodes.

The methods of making and using the electrochemical sensor are also disclosed. The method of making the device includes the steps of positioning at least two spaced apart electrically conductive electrodes in a mold, before or after molding treating at least one of the electrodes with one or more chemicals to change the electrical properties of the treated electrode upon contact with a fluid sample, and molding a body of insulative material with two ends around the electrodes with one end having therein means for receiving a fluid sample. As before, the body is molded in two pieces, with a body and end cap for attaching to one another after the molding is completed, or in a single, unitary piece.

BRIEF DESCRIPTION OF THE DRAWINGS

In the accompanying drawings forming part of the specification, and in which like numerals are employed to designate like parts throughout the same.

FIG. 11 is a sectional end view of the electrochemical sensor of FIG. 7 taken along plane 11—11; and, FIG. 12 is a sectional end view of the electrochemical sensor of FIG. 7 taken along plane 12—12.

DETAILED DESCRIPTION

While this invention is susceptible of embodiments in many different forms, there is shown in the drawings and will herein be described in detail preferred embodiments of the invention with the understanding the present disclosure is to be considered as an exemplification of the principles of the invention and is not intended to limit the broad aspect of the invention to the embodiments illustrated.

The First Embodiment

Figure 1:
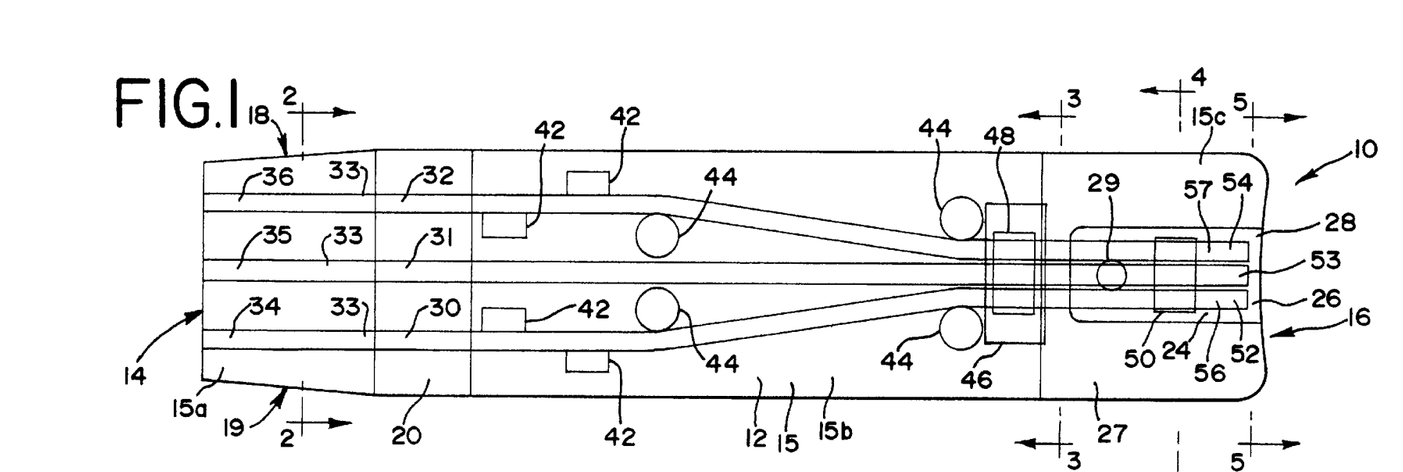
FIG. 1 is an enlarged top plan view of a first embodiment of an electrochemical sensor made in accordance with the teachings of the present invention.
Figure 2:
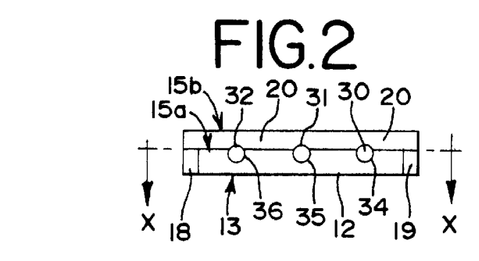
FIG. 2 is a sectional end view of the electrochemical sensor of FIG. 1 taken along plane 2—2.
Figure 3:
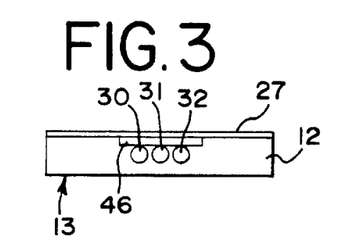
FIG. 3 is a sectional end view of the electrochemical sensor of FIG. 1 taken along plane 3—3.
Figure 4:
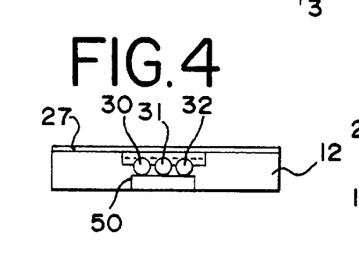
FIG. 4 is a sectional end view of the electrochemical sensor of FIG. 1 taken along plane 4—4.
Figure 5:
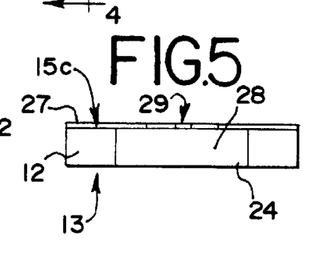
FIG. 5 is a sectional end view of the electrochemical sensor of FIG. 1 taken along plane 5—5.
Figure 6:
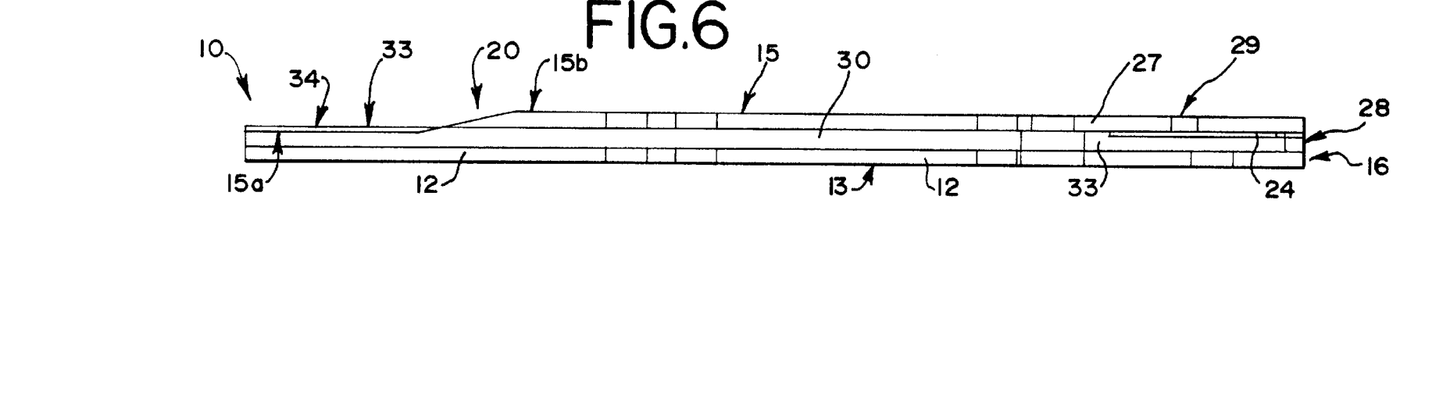
FIG. 6 is a sectional side view of the electrochemical sensor of FIG. 1 taken along plane 6—6.

Referring to FIGS. 1–6, an electrochemical sensor in accordance with the present invention, first embodiment, is depicted. FIG. 1 shows the sensor 10 as though it were made out of clear plastic, permitting one to look inside it. As discussed herein, the internal components and hidden external components would not normally be visible looking down on the sensor 10. This rendition would be similar to a view taken along plane x—x in FIG. 2.

The sensor or test strip of the first embodiment 10 includes an injection molded plastic body 12, opaque or preferably translucent, having a meter attachment end or plug end 14 and a fluid sample receiving end 16. The body has a bottom surface 13, a top surface 15 and a tapered portion 20 connecting a first top surface 15a to a second top surface 15b, the first top surface being lower than the second top surface, and a third top surface 15c, also lower than the second top surface. The body 12 contains three spaced apart electrodes 30,31,32. The plug end 14 of the body 12 includes a pair of tapered side edges 18,19 and a wedge shaped top portion 20. The tapered side edges 18,19 facilitate a user inserting the sensor's plug end 14 into the socket cavity of a conventional meter (not shown). Moreover, the wedged portion 20 of the sensor serves as a stop, and frictionally holds the sensor 10 within the socket cavity of the meter.

The fluid sample receiving end 16 of the sensor 10 includes an electrochemical reaction zone 24 adjacent the terminal end 16 of the body. This reaction zone 24 is a channel formed in the third top surface 15c and about/adjacent the electrodes 30,31,32 in the body 12 for reacting with the fluid drawn into the body 12. While the reaction zone may be formed above or below the electrodes, the preference has been to construct it above the electrodes. An end cap 27 is welded [by ultrasonics or adhesive] over the reaction zone 24 and onto the third top surface 15c. The top of the end cap 27 aligns with the top 15,15b of the body 12. The end cap 27 is preferably made of the same material as the molded body 12 and attached thereto by ultrasonic welding or gluing.

While the cap 27 is shown as a separate piece, it can also be constructed as part of the body 12 and hingably connected to the body such that it can be pivoted onto the third top surface 15c and attached [e.g., see The Second Embodiment]. In this manner, the entire sensor can be made at one time and as one molded, unitary piece.

A capillary opening 28 is formed in the terminal end 16 of the sensor 10 when the cap 27 is welded (or folded) to the body 12 . This capillary opening leads to the reaction zone 24. Preferably, the sensor 10 is a capillary fill device, that is, the reaction zone 24 is small enough to draw a fluid sample into the zone when the capillary opening or inlet 28 is placed in contact with the fluid being tested, such as a drop of blood. Accordingly, if one wants to test his/her blood, s/he touches the terminal end 26 to the blood and the blood is drawn into the sensor 10 and reaction zone 24 through the capillary opening 28. This is much easier than placing the sample (such as blood) on the sensor and on a target zone as in the prior art. To effectuate the capillary effect with the capillary opening 28 to the reaction zone 24, a vent 29 is constructed into the cap 27. This vent is in communication with the reaction zone 24. This vent 29 releases air pressure as the reaction zone 24 draws and fills with fluid. For additional discussion regarding capillary filling, see U.S. Pat. Nos. 4,254,083; 4,413,407; 4,473,457; 5,798,031; 5,120,420; and 5,575,895, the disclosures of which are hereby incorporated by reference.

Mostly encased within the injection molded body 12 are a plurality of electrically conductive leads or electrodes 30,31,32. Preferably, the body 12 is molded about these leads 30,31,32. As noted, these leads are spaced from one another. They 30,31,32 are primarily encased in the body 12 and run from the plug end 14 to the reaction zone 24, just before the terminal end 16. The leads' 30,31,32 ends 26 are positioned just before the terminal end 16 of the sensor.

The conductive leads 30,31,32 consist of an electrically conductive material like metal or metal alloy such as platinum, palladium, gold, silver, nickel, nickel-chrome, stainless steel, copper or the like. Moreover, each lead preferably consists of a single wire, or in an alternative preferred embodiment (See The Second Embodiment), a stamped metal member plated with gold or the like. In the first embodiment, the outer leads 30 and 32 are equally spaced from the inner lead 31 with the spacing of the leads at the fluid sample receiving end 16 of the body 12 being closer together than at the meter attachment end 14.

Segments 33 of the leads 30,31,32 are exposed about the plug end 14 of the body 12 to provide contact surface areas 34,35,36 respectively with the meter (not shown). Preferably, the exposed contact surface areas 34,35,36 extend from the tapered top portion 20 of the body 12 to the plug end 14 of the body 12 on or partially embedded into the first top surface 15a. Specifically, the body 12 may be molded such that the segments 33 of the leads 31,31,32 are embedded (partially molded into the first top surface 15a) and held by the body 12 opposite the contact surface areas 34,35,36. In this manner, the leads are exposed for contact with the meter and maintained in a position without the use of adhesives or welding.

The portion of the leads 30,31,32 between the sensor plug end 14 and the fluid sample receiving end 16 are embedded within the plastic injection molded body 12. Accordingly, the body 12 is constructed of an electrically insulating injection moldable plastic.

Certain structural support components are molded within the body 12 of the sensor 10 to hold and maintain the leads 30,31,32 within the body, in spaced relationship to one another, during and after the molding process. Specifically, guide blocks 42 and alignment pins 44 are molded within the body 12 for proper mounting of the leads 30,31,32. Apertures are also formed in the top surface 15 and bottom surface 13 of the body 12 for permitting the ingress and egress of fingers into the mold during the molding process (to be discussed below). In particular, a first aperture 46 is molded into the second top surface 15b and a second aperture 48 and third aperture 50 are formed into the bottom surface 13 of the body 12. Once the molding is completed, each of these apertures 46,48,50 can be covered up with plastic (e.g., the same plastic used in the molding process) or left open. Their 46,48,50 sizes are relatively small; leaving them open should not cause any safety issues or affect the sensor's ability. Fingers cannot fit into the apertures and debris from the outside will likely be unable to enter the apertures and contact the leads 30,31,32.

Within the reaction zone 24, one lead 30 serves as a primary working electrode 52, a second lead 31 acts as a reference or counter electrode 53, and the third lead 32 serves as an auxiliary, secondary or second working electrode 54. Desirably, the conductive leads 30,31,32 (or electrodes 52,53,54) are the only leads (electrodes) coming into contact with the test sample of fluid entering the sensor 10. The electrodes 52,53,54 are electrically insulated from the rest of the sensor 10 by molded plastic to ensure a signal carried by the leads arises only from that portion exposed to the test sample in the electrochemical reaction zone 24.

In the embodiment, an enzyme 56 is applied to the outer surface of the primary working electrode 52 and, if desired, an electron transfer mediator. The enzyme can consist of, for instance, flavo-proteins, pqq-enzymes, haem-containing enzymes, oxidoreductase, or the like. For additional discussion regarding mediators, see U.S. Pat. Nos. 4,545,382 and 4,224,125, the disclosures of which are hereby incorporated by reference. In an alternative embodiment, an antibody 57 can be applied to the outer surface of the secondary working electrode 54. As such, the reaction zone 24 can contain antibodies, enzyme-antibody conjugates, enzyme-analyte conjugates, and the like. It should be noted that an enzyme 56 can also be applied to the second working electrode 54 and an antibody can be applied to the outer surface of the primary working electrode 52.

As will be appreciated by those having skill in the art, the enzyme 56 is specific for the test to be performed by the sensor 10. For instance, the working electrode 52, or secondary working electrode 54, or both, can be coated with an enzyme 56 such as glucose oxidase or glucose dehydrogenase formulated to react at different levels or intensities for the measurement of glucose in a human blood sample. Thus, as an individual's body glucose concentration increases, the enzyme 56 will make more products. The glucose sensor is used with a meter to measure the electrochemical signal, such as electrical current, arising from oxidation or reduction of the enzymatic turnover product(s). The magnitude of the signal is directly proportional to the glucose concentration or any other compound for which a specific enzyme has been coated on the electrodes.

In an embodiment, the enzyme 56 can be applied to the entire exposed surface area of the primary electrode 52 (or secondary electrode 54). Alternatively, the entire exposed area of the electrode may not need to be covered with the enzyme as long as a well defined area of the electrode is covered with the enzyme.

In a further embodiment and as shown in the prior art, an enzyme 57 can be applied to all the electrodes 52,53,54 in the reaction zone 24 and measures can be taken by a meter.

In the preferred embodiment, one of the working electrodes (52 or 54) is selectively coated with the enzyme 57 carrying a reagent with the enzyme and the other working electrode (54 or 52) is coated with a reagent lacking the respective enzyme. As such, with a meter, one can simultaneously acquire an electrochemical signal from each working electrode and correct for any "background noise" arising from a sample matrix. Thus, the potential or current between the reference and the electrode without the enzyme can be compared with the potential or current between the reference and the electrode with the enzyme. The measuring and comparing of the potential and current differences are well known to those skilled in the art.

As indicated above, the sensor 10 is used in conjunction with a meter capable of measuring an electrical property of the fluid sample after the addition of the fluid sample into the reaction zone 24. The electrical property being measured may be, for example, electrical current, electrical potential, electrical charge, or impedance. An example of measuring changes in electrical potential to perform an analytical test is illustrated by U.S. Pat. No, 5,413,690, the disclosure of which is hereby incorporated by reference.

An example of measuring electrical current to perform an analytical test is illustrated by U.S. Pat. Nos. 5,288,636 and 5,508,171, the disclosures of which are hereby incorporated by reference.

The plug end 14 of the sensor 10 can be inserted and connected to a meter, which includes a power source (a battery). Improvements in such meters and a sensor system are found in U.S. Pat. Nos. 4,999,632; 5,243,516; 5,366,609; 5,352,351; 5,405,511; and 5,438,271, the disclosures of which are hereby incorporated by reference.

Many analyte-containing fluids can be analyzed by the electrochemical sensor of the present invention. For example, analytes in human and animal body fluids, such as whole blood, blood serum and plasma, urine and cerebrospinal fluid may all be measured. Also, analytes found in fermentation products, food and agricultural products, and in environmental substances, which potentially contain environmental contaminants, may be measured.

The Molding Process

In the past, while recognized for its strength and durability, plastic injection molding of sensors has been difficult and thus avoided. One reason is the reluctance to mold around the conductive wires or plates. The industry choice has been to make such sensors like sandwiches, having a top and bottom piece with the insides (conductive elements) being formed on one of the pieces or placed between the pieces. The sandwich-like sensor is then assembled together and sealed closed, such as with an adhesive.

The present invention molds the sensors with the conductive elements inside the mold during the molding process. The advantages are many. In addition to making a stronger more durable sensor, such a process reduces labor involvement and steps and produces a more consistent product.

While multiple sensors 10 can be produced with one mold, the making of a single sensor will be discussed. The mold has the shape of the body 12. The conductive wires 30,31,32 for the electrodes are first molded into the product. Specifically, the wire leads are fed into the mold and placed on or between figures [not shown] projecting into the mold through the openings in the mold (corresponding to the apertures 46,48,50) to hold the wires in place and level during the set-up and molding process. In particular, the bottom apertures permit the fingers projecting into the mold to support the wires and the top apertures permit the fingers projecting into the mold to hold the wires. The liquid plastic is injected into the mold where it fills the mold. The plastic is then cooled.

Once the plastic has formed and hardened, the fingers are pulled from and exit the mold through the openings (apertures 46,48,50). The molded sensor 12 is next ejected from the mold.

The reagents are next applied to the electrodes after the molding process is finished. First, after molding is finished, the cap is treated with a surfactant that facilitates pulling or drawing the fluid (e.g., test blood) into the capillary gap at the end of the sensor. Then, the reagents (including the enzyme) are applied to the electrodes.

The end cap 27 is thereafter connected to the main body 12 and any undesirable openings in the sensor can be sealed closed by the same plastic used for the mold. In the alternative, the chemicals can be applied to the wires after the end cap is married to the body. Any extraneous wire(s) projecting from the sensor can be cut and removed. Then, any desired writings on the sensor (e.g., manufacturing codes, product name, etc.) can then be applied to the sensor by conventional means.

The Second Embodiment

Figure 7:
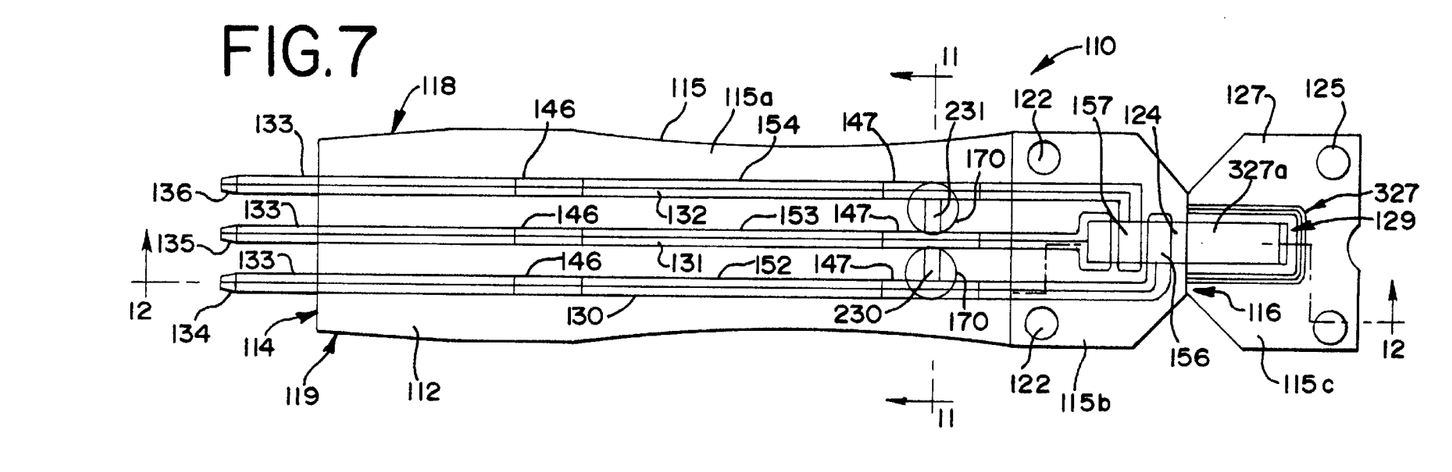
FIG. 7 is an enlarged top plan view of a second embodiment of an electrochemical sensor made in accordance with the teachings of the present invention.
Figures 8, 9:
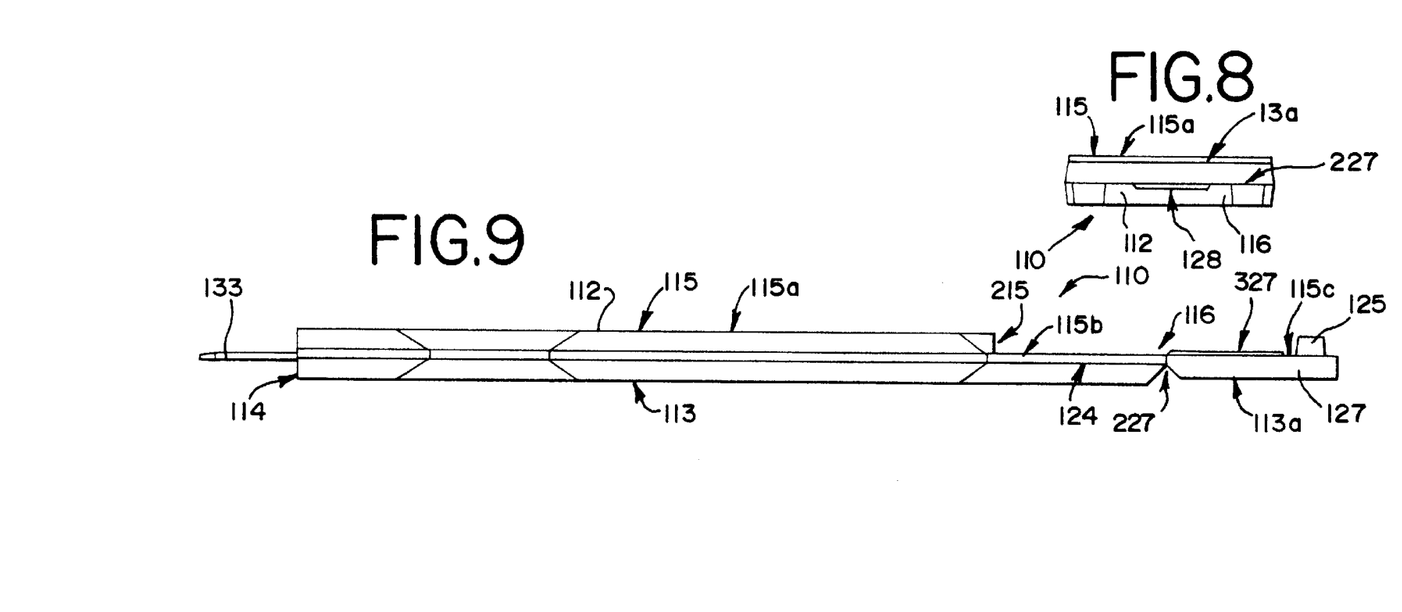
FIG. 8 is an end elevation view of the electrochemical sensor of FIG. 7.
FIG. 9 is a side elevation view of the electrochemical sensor of FIG. 7.

Referring to FIGS. 7–12, an electrochemical sensor in accordance with the present invention, second embodiment, is depicted. In these figures, components similar to those in the first embodiment (10) will be identified with the same reference numbers, but in the 100 series. Specifically, FIG. 7 shows the sensor 110 as though it were made out of clear plastic, permitting one to look inside it. As noted previously, the internal components and hidden external components would not normally be visible looking down on the sensor 110. The sensor of the second embodiment 110 includes a molded plastic body 112 having a meter attachment end or plug end 114 and a fluid sample receiving end 116. The body has a bottom surface 113 and a top surface 115. An end cap 127 is integral to the body 112 and molded with the body. A hinge 227 permits the pivoting of the end cap onto the main body as will be explained. Specifically, the top surface 115 of the sensor 110 has three top surfaces 115a,115b,115c. The first top surface 115a runs most of the length of the body and terminates at a ledge 215; the second top surface 115b is positioned below or is lower than the first 115a; and, the third top surface 115c is separated from the other two top surfaces 115a, 115b by the hinge 227. During construction of the sensor 110, the end cap 127 is rotated about the hinge such that the third top surface 115c abuts the second top surface 115b, face-to-face, and rests adjacent the ledge 215 of the top surface 115a. The bottom surface 13a of the cap 127 thus becomes the top surface adjacent the first top surface 115a. See FIG. 8. A pair of tapered protuberances 125 formed in the end cap 127 and a pair of tapered troughs 122 formed in the main body 112 align and mate when the cap is folded into place. This facilitates and ensures correct alignment of the hinged parts.

The body 112 contains three spaced apart electrodes 130,131,132. The plug end 114 of the body 112 includes a pair of tapered side edges 118,119 to facilitate a user inserting the sensor's plug end 114 into the socket cavity of a conventional meter (not shown).

The fluid sample receiving end 116 of the sensor 110 includes an electrochemical reaction zone 124 adjacent the terminal end 116 of the body. This reaction zone 124 is a channel formed in the second top surface 115b and about/adjacent the electrodes 130,131,132 in the body 112 for reacting with the fluid drawn into the body 112. While this reaction zone may be formed above or below the electrodes, the preference has been to construct it above the electrodes. A ridge 327 is formed on the top surface (third top surface 115c) of the end cap. This ridge prevents any fluid from leaving the reaction zone 124 or debris from entering the reaction zone once the end cap 127 is welded [by ultrasonics or adhesive] onto the second top surface 115b. When the end cap is folded, it is welded into position along the side surfaces of the piece 110. Thus, the ridge can be collapsed during welding and not affect the performance of the sensor. An optional channel 327a may be constructed in the third top surface 115c to increase the height of the reaction zone 124.

A capillary opening 128 is formed in the terminal end 116 of the sensor 110 when the cap 127 is folded and welded into place. This capillary opening leads to the reaction zone 124. The width of the opening 128 is approximately the same as the length of the sensing electrodes 130,131,132 exposed to the test fluid in the reaction zone 124. The sensor 110 of the second embodiment is also a capillary fill device, that is, the reaction zone 124 is small enough to draw a fluid sample into the zone when the capillary opening 128 is placed in contact with the fluid being tested. A vent 129 provided in the cap 127 is in communication with the reaction zone 124 to release pressure as the reaction zone 124 draws and fills with fluid. Preferably, the bottom or base of the capillary inlet is flush with the top surface of electrodes 130,131,132.

Mostly encased within the injection molded body 112 is an electrically conductive plate (stamped or cast) having leads or electrodes 130,131,132. The body 112 is molded around the plate and these leads 130,131,32. The conductive plate is a single piece of material; it includes the leads 130,131,132 and connecting segments 230 and 231. When the sensor is made, the segments are connecting the leads. After molding, the segments 230,231 are cut and/or removed so that the leads are distinct and separated from one another. If they were connected, the system would short circuit.

The electrodes 130,131,132 are primarily encased in the body 112 and run from the plug end 114 into the reaction zone 124, just before the terminal end 116. The leads 130,131,132 may be widened if desired in the reaction zone to expose more surface area to the fluid and chemicals contacting one another in the zone. The leads 130,131,132 can be as wide as the sensing parts. These leads 130,131,132 are an electrically conductive material like metal or metal alloy such as platinum, palladium, gold, silver, nickel, nickel-chrome, stainless steel, copper or the like. To enhance their performance and sensitivity, they may also be coated, e.g., made of copper and coated with gold. In the second embodiment, the leads 130,131,132 are spaced from and parallel to one another.

Segments 133 of the leads 130,131,132 extend outwardly from the body 112 from the plug end 114 of the sensor 110 and are exposed to provide contact surface areas 134,135, 136 respectively with the meter (not shown). These leads can also be embedded in the molded plastic such that their upper surfaces are exposed in portions.

As before, the portion of the leads 130,131,132 between the sensor plug end 114 and the fluid sample receiving end 116 are embedded, or encased, within the plastic injection molded body 112; the body 112 is constructed of an electrically insulating injection moldable plastic.

Figure 10:
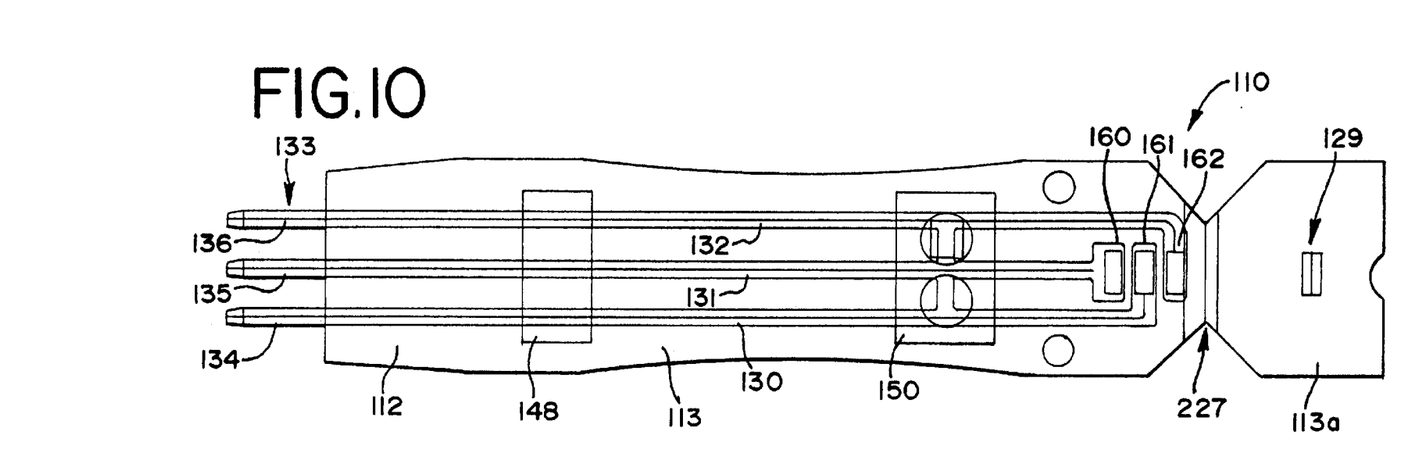
FIG. 10 is a bottom plan view of the electrochemical sensor of FIG. 7.
Figures 11, 12:
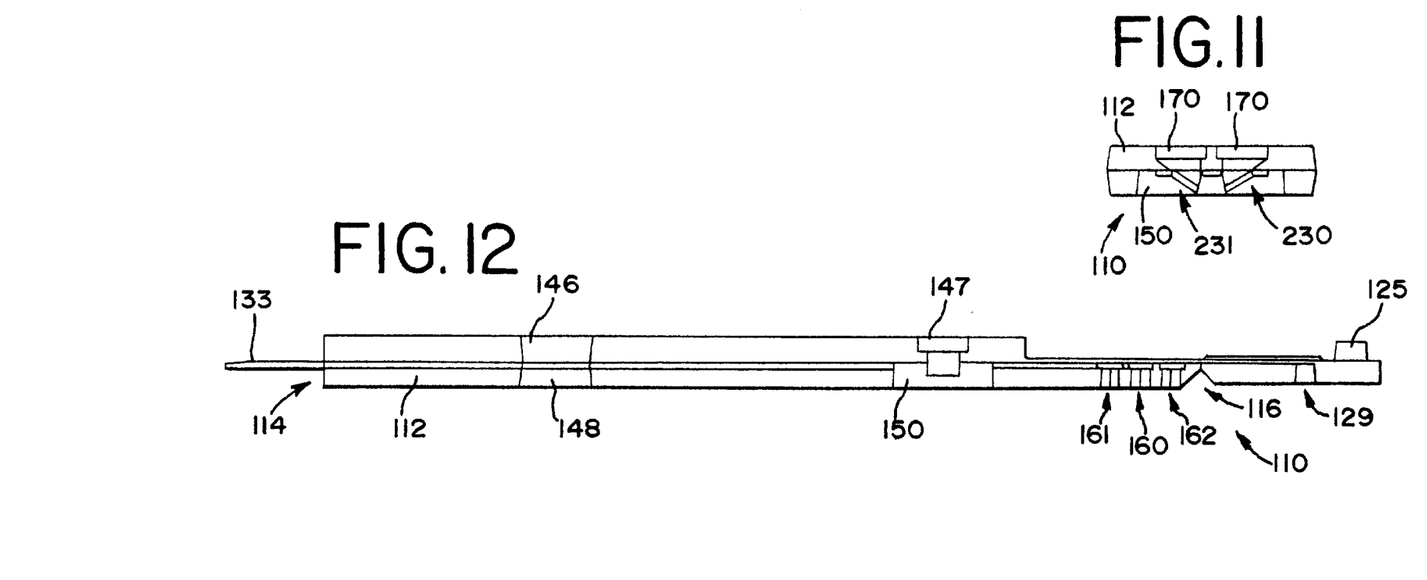

Apertures are formed in the top surface 115 and bottom surface 113 of the body 112 for permitting the ingress and egress of fingers into the mold during the molding process. In particular, a set (3) of first apertures 146 and a set (3) of second apertures 147 are molded into the top surface 15a; a third aperture 148 and fourth aperture 150 and a set (3) of fifth apertures 160,161,162 are formed into the bottom surface 113 of the body 112. Once the molding is completed, each of these apertures 146,147,148,150 can be covered up with plastic (e.g., the same plastic used in the molding process) or left open.

Within the reaction zone 124, one outer lead 130 serves as a primary working electrode 152, the center lead 131 acts as a reference or counter electrode 153, and the other outer lead 132 serves as an auxiliary or secondary or second working electrode 154. These conductive leads 130,131,132 (or electrodes 152,153,154) are the only leads (electrodes) coming into contact with the test sample of fluid entering the sensor 110. The electrodes 152,153,154 are electrically insulated from the rest of the sensor 110 by molded plastic to ensure a signal carried by the leads arises only from that portion exposed to the test sample in the electrochemical reaction zone 124.

As with the first embodiment, an enzyme 156 is applied to the outer surface of the primary working electrode 152 and, if desired, an electron transfer mediator. An antibody 157 may also be applied to the outer surface of the secondary working electrode 154. An enzyme 156 can also be applied the second working electrode 154 and an antibody to the outer surface of the primary working electrode 52.

The enzyme 156 can be applied to the entire exposed surface area of the primary electrode 152 (or secondary electrode 154). Alternatively, the entire exposed area of the electrode may not need to be covered with the enzyme as long as a well defined area of the electrode is covered with the enzyme. Or, an enzyme can be applied to all the electrodes 152,153,154 in the reaction zone 124 and measurements can be taken by a meter. Preferably, one of the working electrodes (152 or 154) is selectively coated with the enzyme carrying a reagent with the enzyme and the other working electrode (154 or 152) is coated with a reagent lacking the respective enzyme.

The sensor 110 is used in conjunction with a meter capable of measuring an electrical property of the fluid sample after the addition of the fluid sample into the reaction zone 124. The plug end 114 of the sensor 110 is inserted and connected to a meter, as before with the first embodiment.

The Molding Process

The mold has the shape of the body 112. The conductive 130,131,132 leads/electrodes (in the form of a plate with the joining extensions 230,231 for the electrodes) are first treated with any coatings (metal). The chemicals/reagents (with and without enzymes) may also be applied before molding; or, they can be applied after the molding. The plate is fed into the mold and placed on or between fingers (not shown) projecting into the mold through the openings in the mold (corresponding to the apertures 146,147,148,150) to hold the plate in place and level during the set-up and molding process. Knives or punches (not shown) are also inserted through the top surface of the mold (outline of opening formed by the knives/punches 170). These knives punch and sever the jointing extensions 230,231 and hold the bent portions in place during molding (see FIG. 11). As before, the bottom apertures permit the fingers projecting into the mold to support the plate with leads and the top apertures permit the fingers projecting into the mold to hold the plate and leads. The liquid plastic is injected into the mold where it fills the mold. The plastic is then cooled.

Once the plastic has formed and hardened, the fingers are drawn from the mold through the openings (apertures 146, 147,148,150,160,161,162). The knives/punches are drawn through the upper surface openings 170. Once the knives/punches are removed, the cut or skived extensions 230,231 disposed between the leads 130,131 and 131,132 ensures the leads are kept separate. The molded sensor 112 is then ejected from the mold and any undesirable openings in the sensor can be sealed closed by the same plastic used for the mold. In the preferred alternative, the critical reagents are applied to the sensors in the reaction zone 124 above the leads. A surfactant can be used to treat the capillary inlet to facilitate the capillary function. Any extraneous metal projecting from the sensor can be cut and removed. Then, any desired writings on the sensor (e.g., manufacturing codes, product name, etc.) can then be applied to the sensors by conventional means.

While the specific embodiments have been illustrated and described, numerous modifications come to mind without significantly departing from the spirit of the invention and the scope of protection is only limited by the scope of the accompanying claims. For instance, in another embodiment of the present invention, a sensor is designed for use with a light reflectance measuring meter for photometric detection of a die contained within a fluid sample receiving well.

We claim:

1. An electrochemical device for cooperating with an electronic meter capable of measuring electrical properties between at least two electrically conductive electrodes, comprising:

at least two spaced apart electrically conductive electrodes;

a unitary body of one piece molded plastic insulative material with two ends housing the electrodes with a hinge constructed in the body permitting the pivoting and connecting of a portion of the body onto itself;

means for connecting the meter to the body;

means for receiving a fluid sample at one end of the body; and, one or more substances on at least one of the electrodes to change the electrical properties between the electrodes upon contact with the fluid sample.

2. The electrochemical device of claim 1 wherein at least one protuberance is formed in a portion of the body located on one side of the hinge and at least one trough is formed in a portion of the body located on the other side of the hinge for mating with the at least one protuberance when the one side is folded onto the other side about the hinge.

3. The electrochemical device of claim 1 wherein two tapered protuberances are formed in the portion of the body located on the one side of the hinge and two tapered troughs are formed in the portion of the body located on the other side of the hinge for mating with the two protuberances when the one side is folded onto the other side about the hinge.

4. The electrochemical device of claim 1 wherein a capillary inlet adapted to draw the fluid sample into the body upon contact with the fluid sample is formed at the hinge.

5. An electrochemical device for cooperating with an electronic meter capable of measuring electrical properties between at least two electrically conductive electrodes, comprising:
   at least two spaced apart electrically conductive electrodes;
   a unitary single piece body of molded plastic insulative material with two ends housing the electrodes with the electrodes molded into and at least partially encased by the plastic;
   means for connecting the meter to the body;
   means for receiving a liquid sample at one end of the body; and,
   one or more substances on at least one of the electrodes to change the electrical properties between the electrodes upon contact with the liquid sample.

6. The electrochemical device of claim 5 wherein an enzyme is on one of the electrodes and an antibody is on another of the electrodes.

7. The electrochemical device of claim 6 wherein an electron mediator is on the outer surface of one or more of the electrodes.

8. An electrochemical device for cooperating with an electronic meter capable of measuring electrical properties between at least two electrically conductive electrodes, comprising:
   at least two spaced apart electrically conductive electrodes;
   a unitary single piece body of insulative material with two ends and encasing a part of the electrodes;
   means for connecting the meter to the body;
   a capillary inlet adapted to draw the fluid sample into the body upon contact with the fluid sample at one end of the body; and,
   one or more substances on at least one of the electrodes to change the electrical properties between the electrodes upon contact with the fluid sample.

9. The electrochemical device of claim 8 wherein the capillary inlet is molded into the end of the body and is in communications with a reaction zone.

10. The electrochemical device of claim 9 wherein the reaction zone is a channel formed in the body above the electrodes adapted for reacting with the fluid drawn into the body by the capillary force.

11. The electrochemical device of claim 10 wherein the capillary inlet has a vent in communications therewith for relieving pressure.

12. An electrochemical device for cooperating with an electronic meter capable of measuring electrical properties between at least two electrically conductive electrodes, comprising:
   at least two spaced apart electrically conductive wires;
   a unitary single piece body of insulative material with two ends and encasing a part of the conductive wires;
   means for connecting the meter to the body;
   means for receiving a liquid sample at one end of the body; and,
   one or more substances on at least one of the conductive wires to change the electrical properties between the wires upon contact with the liquid sample.

13. The electrochemical device of claim 12 wherein at least one wire is coated with a different conductive material than the composition of the wire.

14. An electrochemical device for cooperating with an electronic meter capable of measuring electrical properties between at least two electrically conductive electrodes, comprising:
   at least two spaced apart electrically conductive electrodes formed from a conductive plate;
   a unitary single piece body of insulative material with two ends and encasing a part of the electrodes;
   means for connecting the meter to the body;
   means for receiving a liquid sample at one end of the body; and,
   one or more substances on at least one of the electrodes to change the electrical properties between the electrodes upon contact with the liquid sample.

15. The electrochemical device of claim 14 wherein at least one electrode is coated with a different conductive material than the composition of the conductive plate.

16. An electrochemical device for cooperating with an electronic meter capable of measuring electrical properties between electrically conductive electrodes, comprising:
   three spaced apart electrically conductive electrodes;
   a body of insulative material with two ends housing the electrodes, the body composed of two pieces, a body and an end cap, attached to one another with each piece being made of molded plastic;
   means for connecting a meter to the body;
   means for receiving a fluid sample at one end of the body; and,
   one or more substances on at least one of the electrodes to change the electrical properties between the electrodes upon contact with the fluid sample.

17. An electrochemical device for cooperating with an electronic meter capable of measuring electrical properties between electrically conductive electrodes, comprising:
   three spaced apart electrically conductive electrodes;
   a body of insulative material with two ends housing the electrodes and a hinge constructed in the body permitting the pivoting arid connecting of a portion of the body onto itself with at least one protuberance formed in a portion of the body located on one side of the hinge and at least one trough formed in a portion of the body located on the other side of the hinge for mating with the at least one protuberance when the one side is folded onto the other side about the hinge;
   means for connecting a meter to the body;
   means for receiving a fluid sample at one end of the body; and,
   one or more substances on at least one of the electrodes to change the electrical properties between the electrodes upon contact with the fluid sample.

18. The electrochemical device of claim 17 wherein a capillary inlet adapted to draw the fluid sample into the body upon contact with the fluid sample is formed at the hinge.

19. An electrochemical device for cooperating with an electronic meter capable of measuring electrical properties between electrically conductive electrodes, comprising:

three spaced apart electrically conductive electrodes;

a unitary single piece body of molded plastic insulative material with two ends housing the electrodes, a part of the electrodes partially encased and molded into the plastic;

means for connecting a meter to the body;

means for receiving a liquid sample at one end of the body; and, one or more substances on at least one of the electrodes to change the electrical properties between the electrodes upon contact with the liquid sample.

20. The electrochemical device of claim 19 wherein an enzyme is on one of the electrodes and an antibody is on another of the electrodes.

21. The electrochemical device of claim 20 wherein an electron mediator is on the outer surface of one or more of the electrodes.

22. An electrochemical device for cooperating with an electronic meter capable of measuring electrical properties between electrically conductive electrodes, comprising:

three spaced apart electrically conductive electrodes;

a unitary single piece body of insulative material with two ends and encasing at least a part of the electrodes;

means for connecting a meter to the body;

a capillary inlet adapted to draw the fluid sample into the body upon contact with the fluid sample; and, one or more substances on at least one of the electrodes to change the electrical properties between the electrodes upon contact with the fluid sample.

23. The electrochemical device of claim 22 wherein the capillary inlet is molded into the end of the body and is in communications with a reaction zone, the reaction zone being a channel formed in the body above the electrodes adapted for reacting with the fluid drawn into the body by the capillary force and in communications with a vent for relieving pressure.

24. An electrochemical device for cooperating with an electronic meter capable of measuring electrical properties between electrically conductive electrodes, comprising:

three spaced apart electrically conductive electrodes, the electrodes being one of either conductive wires or formed from a conductive plate;

a unitary single piece body of insulative material with two ends and encasing at least part of the electrodes;

means for connecting a meter to the body;

means for receiving a liquid sample at one end of the body; and, one or more substances on at least one of the electrodes to change the electrical properties between the electrodes upon contact with the liquid sample.

25. An electrochemical device for measuring an analyte by cooperating with an electronic meter capable of measuring the electrical properties between at least two electrically conductive electrodes, comprising:

at least two spaced apart electrically conductive electrodes;

a unitary, single piece molded plastic body with two ends housing the electrodes and encasing at least a part of the electrodes molded therein;

a plug formed at one end of the body exposing the electrodes outside the body for connecting the meter to the body;

a capillary inlet adapted to draw the fluid sample into the body upon contact with the fluid sample at the other end of the body;

one or more substances on at least one of the electrodes to change the electrical properties of the treated electrodes upon contact with the fluid sample.

26. The electrochemical device of claim 25 wherein the capillary inlet is molded into the end of the body and is in communications with a reaction zone, the reaction zone being a channel formed in the body above the electrodes adapted for reacting with the fluid drawn into the body by the capillary force and in communications with a vent for relieving pressure.

27. The electrochemical device of claim 26 wherein the electrodes are one of either conductive wires or formed from a conductive plate.

28. The electrochemical device of claim 25 wherein the one or more substances on at least one of the electrodes to change the electrical properties between the electrodes upon contact with the fluid sample is a coating on at least one electrode with a reagent and an enzyme.

29. The electrochemical device of claim 28 wherein an enzyme is on the outer surface of one of the electrodes.

30. The electrochemical device of claim 29 wherein an antibody is on another of the electrodes.

31. The electrochemical device of claim 30 wherein an electron mediator is on the outer surface of one or more of the electrodes.

32. A sensor comprising:

a body having an end for cooperating with a meter and an end for receiving a fluid sample;

a plurality of electrically conductive leads with at least a part thereof encased by the body and with at least one lead extending into the end for receiving the fluid sample and at least one of the leads being a wire conductor; and, an enzyme on the at least one lead.

33. The sensor of claim 32 wherein all of the leads are wire conductors.

34. The sensor of claim 32 wherein a plurality of guides are molded within the body to prevent the leads from moving within the body.

35. A sensor comprising:

a body having an end for cooperating with a meter and an end for receiving a fluid sample;

a plurality of electrically conductive leads with a part thereof encased by the body and with at least one lead extending into the end for receiving the fluid sample and at least one of the leads being a stamped conductive metal member; and, an enzyme on the at least one lead.

36. The sensor of claim 35 wherein all of the leads are stamped conductive metal members.

37. The sensor of claim 36 wherein at least one of the stamped conductive metal members is coated with another electrically conductive material.

38. The sensor of claim 36 wherein at least a portion of at least two stamped conductive metal members have different geometric shapes.

39. A sensor comprising:

an injection molded plastic body having an attachment end and a fluid sample receiving cavity;

a plurality of electrically conductive leads with at least a part thereof encased by the body and with at least one lead extending from the attachment end to the fluid sample receiving cavity and at least one of the leads being a wire conductor; and, an enzyme within the fluid sample receiving cavity.

40. The sensor of claim 39 wherein a plurality of guides are molded within the body to hold and maintain the leads within the body.

41. The sensor of claim 39 wherein the enzyme is on at least one of the leads.

42. The sensor of claim 41 wherein the enzyme facilitates analyzing analytes within a sample of human body or animal fluid.

43. A sensor comprising:
- an injection molded plastic body having an attachment end and a fluid sample receiving cavity;
- a plurality of electrically conductive leads with at least a part thereof encased by the body and with at least one lead extending from the attachment end to the fluid sample receiving cavity and at least one of the leads being a stamped conductive metal member; and,
- an enzyme within the fluid sample receiving cavity.

44. The sensor of claim 43 wherein the stamped conductive metal member is coated with an electrically conductive material.

45. The sensor of claim 44 wherein the stamped conductive metal member is coated with a different electrically conductive material than the composition of the conductive metal member.

46. A sensor for analyzing a fluid sample comprising:
- an injection molded body having an attachment end and a sample receiving cavity;
- a plurality of electrically conductive leads extending between the attachment end of the body and the sample receiving cavity and being at least partially embedded within the body and at least partially exposed at the attachment end of the molded body and with at least one of the leads extending into the sample receiving cavity, the leads extending into the sample receiving cavity being electrically isolated from the rest of the sensor by the molded plastic, with at least two of the leads including different metals and with at least two of the leads being different sizes;
- a plurality of guides molded within the body with at least one of the guides abutting against at least one of the leads; and,
- a compound within the sample receiving cavity for analyzing the fluid sample, the compound being one of an enzyme, an antibody or a reactive chemical.

47. The sensor of claim 46 wherein the cavity includes a capillary inlet for drawing a fluid sample.

* * * * *

UNITED STATES PATENT AND TRADEMARK OFFICE
CERTIFICATE OF CORRECTION

PATENT NO. : 6,576,102 B1  Page 1 of 3
DATED : June 10, 2003
INVENTOR(S) : Craig Rappin, Kiamars Hajizadeh and Kelly Mills It is certified that error appears in the above-identified patent and that said Letters Patent is hereby corrected as shown below:

Title page,
Item [56], References Cited, U.S. PATENT DOCUMENTS, add the following:

| | | | |
|---|---|---|---|
| 4,224,125 | 9/1980 | Nakamura et al. | 204/195B |
| 4,239,471 | 12/1980 | Swaroop | 425/144 |
| 4,254,083 | 3/1981 | Columbus | 422/55 |
| 4,356,074 | 10/1982 | Johnson | 204/195P |
| 4,376,689 | 3/1983 | Nakamura et al. | 204/195B |
| 4,472,131 | 9/1984 | Ryder | 425/548 |
| 4,473,457 | 9/1984 | Columbus | 204/416 |
| 4,502,660 | 3/1985 | Luther et al. | 249/144 |
| 4,543,326 | 9/1985 | Miyashita et al | 435/15 |
| 4,545,382 | 10/1985 | Higgins et al. | 128/635 |
| 4,634,366 | 1/1987 | Brun et al. | 425/526 |
| 4,717,113 | 1/1988 | Martin | 249/63 |
| 4,758,323 | 7/1988 | Davis et al. | 204/403 |
| 4,765,585 | 8/1988 | Wieder | 249/64 |
| 4,768,747 | 9/1988 | Williams et al. | 249/63 |
| 4,810,633 | 3/1989 | Bauer et al. | 435/25 |
| 4,820,399 | 4/1989 | Senda et al. | 204/403 |
| 4,830,959 | 5/1989 | McNeil et al. | 435/7 |
| 4,832,307 | 5/1989 | Watanabe et al. | 249/63 |
| 4,894,137 | 1/1990 | Takizawa et al. | 204/403 |
| 4,897,173 | 1/1990 | Nankai et al. | 204/403 |
| 4,900,424 | 2/1990 | Birth et al. | 204/409 |
| 4,959,005 | 9/1990 | Sorensen | 425/577 |
| 4,959,305 | 9/1990 | Woodrum | 435/7 |
| 4,999,582 | 3/1991 | Parks et al. | 324/438 |
| 5,015,426 | 5/1991 | Maus et al. | 264/40.5 |
| 5,040,963 | 8/1991 | Beck et al. | 425/130 |
| 5,122,244 | 6/1992 | Hoenes et al. | 204/153.12 |
| 5,139,714 | 8/1992 | Hettinga | 264/45.1 |
| 5,173,165 | 12/1992 | Schmid et al. | 204/403 |
| 5,192,415 | 3/1993 | Yoshioka et al. | 204/403 |
| 5,286,362 | 2/1994 | Hoenes et al. | 204/403 |
| 5,288,636 | 2/1994 | Pollmann et al. | 435/288 |
| 5,346,659 | 9/1994 | Buhler et al. | 264/68 |
| 5,354,447 | 10/1994 | Uenoyama et al. | 204/403 |
| 5,407,344 | 4/1995 | Rombalski, Jr. et al. | 425/190 |
| 5,508,171 | 4/1996 | Walling et al. | 205/777.5 |
| 5,509,410 | 4/1996 | Hill et al. | 128/637 |
| 5,527,173 | 6/1996 | Miller et al. | 425/126.1 |
| 5,560,939 | 10/1996 | Nakagawa et al. | 425/139 |
| 5,575,895 | 11/1996 | Ikeda et al. | 204/403 |
| 5,593,852 | 1/1997 | Heller et al. | 435/14 |
| 5,595,771 | 1/1997 | Foltuz et al. | 425/443 |
| 5,653,934 | 8/1997 | Brun, Jr. et al. | 264/334 |

UNITED STATES PATENT AND TRADEMARK OFFICE
CERTIFICATE OF CORRECTION

PATENT NO. : 6,576,102 B1
DATED : June 10, 2003
INVENTOR(S) : Craig Rappin, Kiamars Hajizadeh and Kelly Mills It is certified that error appears in the above-identified patent and that said Letters Patent is hereby corrected as shown below:

Title page (cont'd),

| | | | |
|---|---|---|---|
| 5,682,884 | 11/1997 | Hill et al. | 128/637 |
| 5,707,662 | 1/1998 | Bright et al. | 425/547 |
| 5,727,548 | 3/1998 | Hill et al. | 128/637 |
| 5,736,173 | 4/1998 | Wright et al. | 425/577 |
| 5,762,770 | 6/1998 | Pritchard et al. | 204/403 |
| 5,798,031 | 8/1998 | Charlton et al. | 204/403 |
| 5,820,551 | 10/1998 | Hill et al. | 600/347 |
| 5,965,380 | 10/1999 | Heller et al. | 435/14 |
| 5,997,817 | 12/1999 | Crismore et al. | 422/58 |
| 6,101,791 | 8/2000 | Louviere | 53/467 |
| 6,143,576 | 11/2000 | Buechler | 436/518 |
| 6,156,270 | 12/2000 | Buechler | 422/58 |
| 6,162,611 | 12/2000 | Heller et al. | 435/14 |
| 6,162,639 | 12/2000 | Douglas | 435/287.1 |
| 6,175,752 | 1/2001 | Say et al. | 600/345 |

FOREIGN PATENT DOCUMENTS, add the following:

| | | |
|---|---|---|
| EP | 0080304 A1 | 06/01/1983 |
| EP | 0127958 A2 | 12/12/1984 |
| EP | 0136362 A1 | 04/10/1985 |
| Japan | 60-173457 | 09/06/1985 |
| Japan | 60-173458 | 09/06/1985 |
| Japan | 60-173459 | 09/06/1985 |
| EP | 0 170 375 A2 | 02/05/1986 |
| EP | 0 171 148 A1 | 002/12/1986 |
| Japan | 61-90050 | 05/08/1986 |
| EP | 0206218 A2 | 12/30/1986 |
| Japan | 63-58149 | 03/12/1988 |
| Japan | 63-128252 | 05/31/1988 |
| Japan | 63-139246 | 06/11/1988 |
| UK | 2204408 A | 11/09/1988 |
| Japan | 63-317757 | 12/26/1988 |
| Japan | 63-317758 | 12/26/1988 |
| Japan | 1-91558 | 04/11/1989 |
| Japan | 1-114746 | 05/08/1989 |
| Japan | 1-114747 | 05/08/1989 |
| Japan | 1-134244 | 05/26/1989 |
| Japan | 1-156658 | 06/20/1989 |
| PCT | WO 89/08713 | 09/21/1989 |
| EP | 0359831 A1 | 03/28/1990 |
| EP | 0 170 375 B1 | 05/16/1990 |
| EP | 0400918 A1 | 12/05/1990 |
| EP | 0 171 148 B1 | 04/17/1991 |

UNITED STATES PATENT AND TRADEMARK OFFICE
CERTIFICATE OF CORRECTION

PATENT NO. : 6,576,102 B1
DATED : June 10, 2003
INVENTOR(S) : Craig Rappin, Kiamars Hajizadeh and Kelly Mills It is certified that error appears in the above-identified patent and that said Letters Patent is hereby corrected as shown below:

Column 12,
Line 49, please delete the word "arid" and insert the word -- and -- therefor Column 13,
Lines 7, 45 and 49, please delete the word "liquid" and insert the word -- fluid -- therefor Signed and Sealed this Seventeenth Day of August, 2004

JON W. DUDAS
*Acting Director of the United States Patent and Trademark Office*